United States Patent [19]

Nishino et al.

[11] 4,141,972

[45] Feb. 27, 1979

[54] PURINE NUCLEOSIDE 5'-PHOSPHATE (MONO, DI OR TRI) 3'(2')-DIPHOSPHATES AND PROCESSES FOR THEIR PREPARATION

[75] Inventors: Toyokazu Nishino, Hikisokita; Yasutaro Hamagishi, Sakai; Toshikazu Oki, Kamakura; Sawao Murao, Sakai, all of Japan

[73] Assignee: Sanraku-Ocean Co., Ltd., Tokyo, Japan

[21] Appl. No.: 791,276

[22] Filed: Apr. 27, 1977

Related U.S. Application Data

[62] Division of Ser. No. 559,462, Mar. 18, 1975, Pat. No. 4,059,487.

[30] Foreign Application Priority Data

Mar. 29, 1974 [JP] Japan .................................. 49-34625
Dec. 16, 1974 [JP] Japan ................................ 49-143546

[51] Int. Cl.$^2$ ....................... A61K 31/70; C07H 19/20
[52] U.S. Cl. ................................. 424/180; 195/28 N; 536/28; 536/29; 424/181
[58] Field of Search ..................... 536/27, 28; 424/180

[56] References Cited

U.S. PATENT DOCUMENTS

| 3,407,190 | 10/1968 | Honjo et al. | 536/28 |
| 3,413,282 | 11/1968 | Yoshikawa et al. | 536/27 |
| 3,423,399 | 1/1969 | Honjo et al. | 536/28 |
| 3,457,254 | 7/1969 | Yano et al. | 536/28 |
| 3,475,409 | 10/1969 | Ouchi et al. | 536/28 |

OTHER PUBLICATIONS

Berger, "Biochimica et Biophysica Acta", vol. 20, 1956, pp. 23-26.

*Primary Examiner*—Johnnie R. Brown
*Attorney, Agent, or Firm*—Frank J. Jordan

[57] ABSTRACT

New purine nucleoside 5'-phosphate (mono, di or tri) 3'(2')-diphosphates and the sodium, lithium and potassium salts thereof are elaborated by the enzymatic transfer of pyrophosphoryl group from ATP (adenosine triphosphate), dATP (deoxyadenosine triphosphate) and pppApp (adenosine 5'-triphosphate 3'(2') diphosphate) to specified 5'-purine nucleotides, and a new nucloetide pyrophosphotransferase used for this enzyme reaction is produced by actinomycetes and other microorganisms and recovered from the culture filtrate and mycelium by the conventional methods for recovering enzymes. These compounds are useful for treating leukemia L1210 in mice.

5 Claims, 9 Drawing Figures

FIG.5
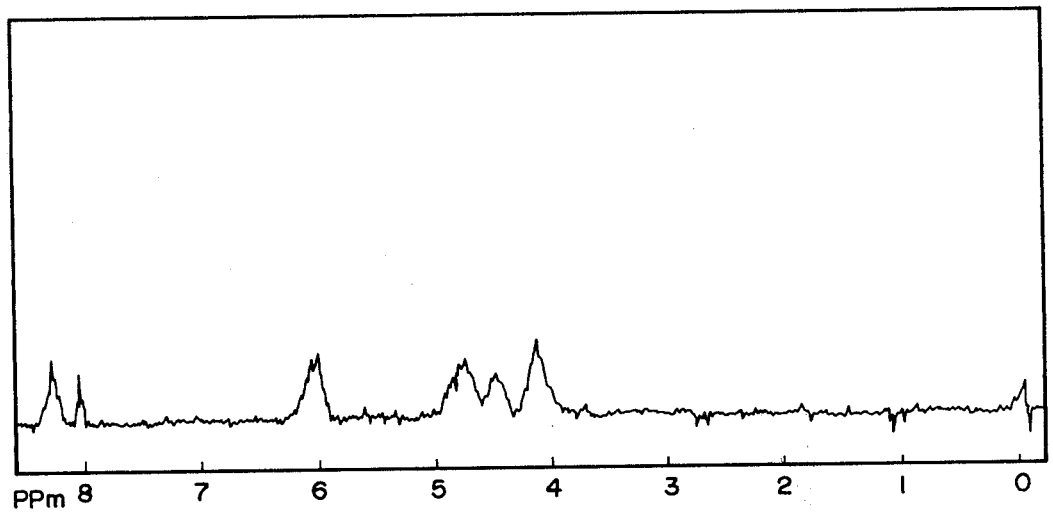
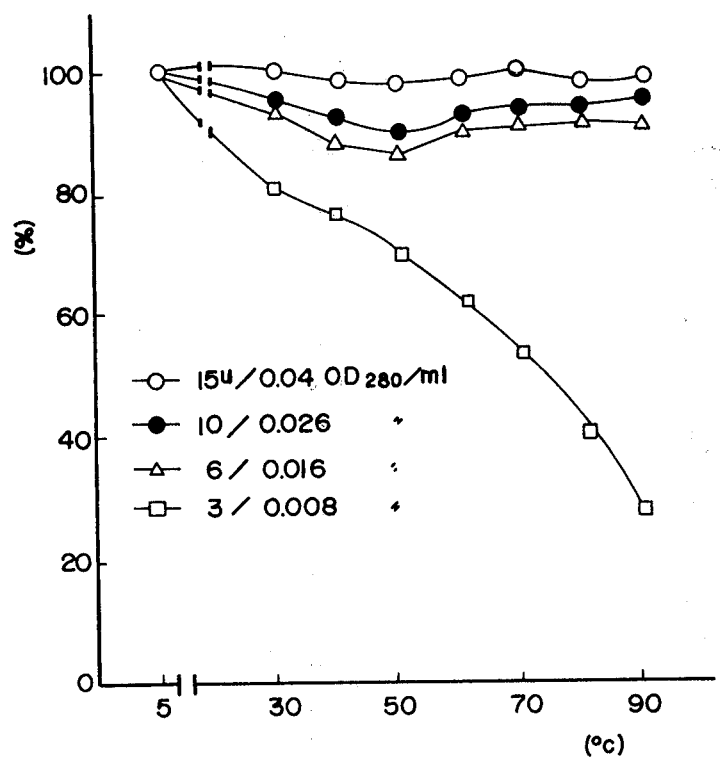
FIG.8

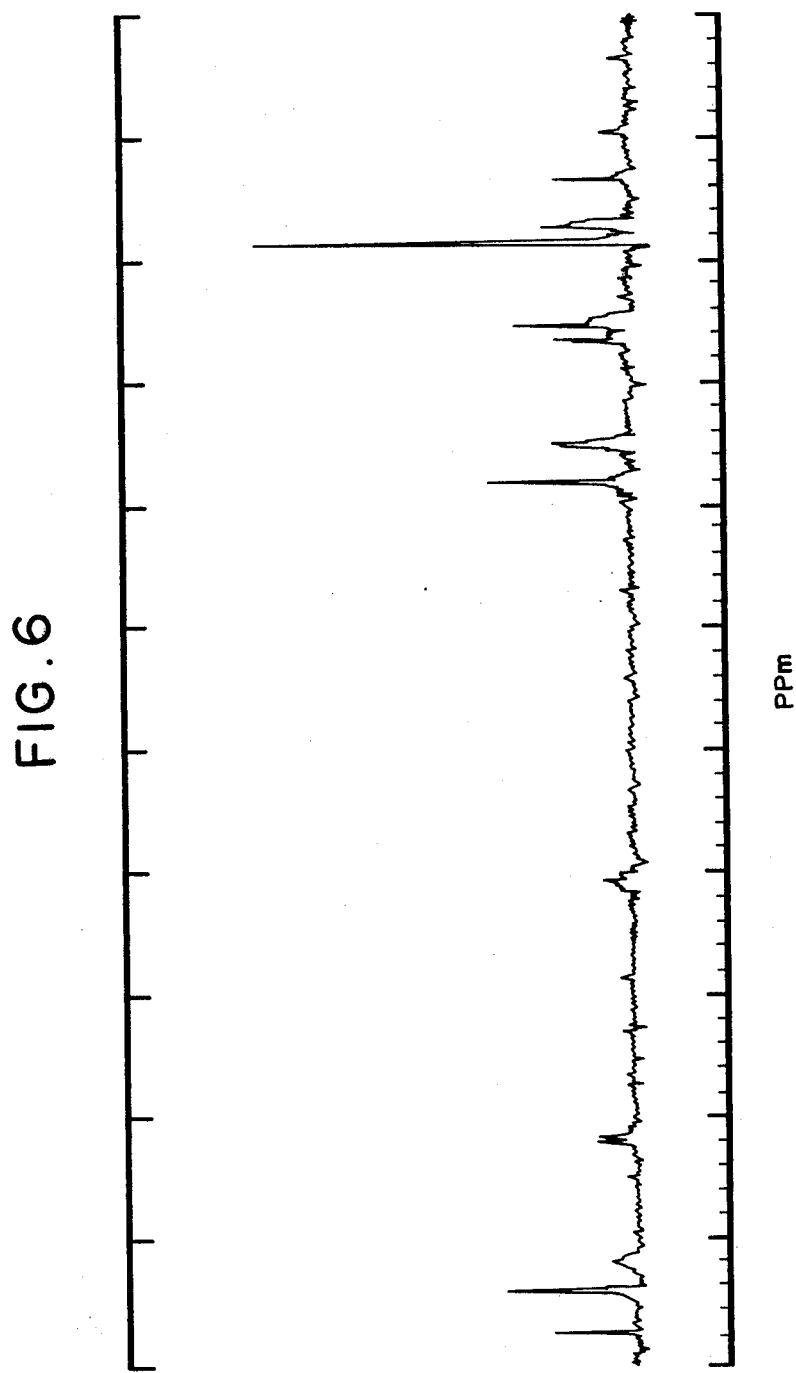

PURINE NUCLEOSIDE 5'-PHOSPHATE (MONO, DI OR TRI) 3'(2')-DIPHOSPHATES AND PROCESSES FOR THEIR PREPARATION

This is a division of application Ser. No. 559,462 filed Mar. 18, 1975 now U.S. Pat. No. 4,059,487.

BACKGROUND OF THE INVENTION

This invention relates to new purine nucleoside 5'-phosphate (mono, di or tri) 3' (2')-diphosphates and the lithium, sodium and potassium salts thereof, and to methods for the production of the purine nucleoside 5'-phosphate (mono, di or tri) 3' (2')-diphosphates. More particularly, it relates to new purine nucleoside 5'-phosphate (mono, di or tri) 3' (2')-diphosphates which are produced by the enzymatic transfer of pyrophosphoryl group from ATP, dATP and pppApp to specified 5'-purine nucleotides using microorganisms belonging to the genera Streptomyces, Actinomyces and Streptoverticillium, or a new nucleotide pyrophosphotransferase thereof, and to processes for the production of the purine nucleoside 5'-phosphate (mono, di or tri) 3' (2')-diphosphates. It also relates to a new nucleotide pyrophosphotransferase, and to the methods for its recovery and purification from the cultured broth and mycelium of microorganisms belonging to the genera Streptomyces, Streptoverticillium and Actinomyces.

As is well known, adenosine tetraphosphate (ppppA), guanosine tetraphosphate (ppGpp) and Guanosine pentaphosphate (pppGpp) are distributed in nature, especially in microorganisms and animals, as unusual nucleoside phosphates. The ppGpp and pppGpp are particularly being watched with keen interest in the regulation of protein and ribonucleic acid syntheses in *E. coli,* and it is expected that they have an important role in glycolysis, lipid synthesis, energy metabolism and phosphorylation of various organisms.

In the present invention, purine nucleoside 5'-phosphate (mono, di or tri) 3' (2')-diphosphate compounds are generalized as the following symbol:

mXpp in which X represents one of the nucleosides selected from adenosine (abbreviated as A), guanosine (abbreviated as G) and inosine (abbreviated as I), and p and p (CH$_2$)p stands for phosphate residue and methylene phosphate residue, respectively. In this specification phosphate residue is also referred to as phosphoryl group.

The notation, m represents a number of phosphoryl groups at the 5'-position of the nucleoside in which m is an integral number from 1 to 3. The p after the X is the 3' (2')-position. The notation 3' (2')- indicates that the position of the phosphoryl group attached to the ribose is either 3'- or 2'- of the ribose, as there is the reversible exchange of the phosphoryl group between the 3'- and the 2'- position of ribose in the nucleoside under a certain condition. For instance, pppApp indicates adenosine 5'-triphosphate 3' (2')-diphosphate and p(CH$_2$)ppGpp is β, γ-methylene guanosine 5'-triphosphate 3' (2')-diphosphate.

However, it is difficult to extract unusual purine nucleoside phosphates such as ppGpp and pppGpp from microorganisms because of a very small distribution therein, and further the chemical synthesis of these nucleoside phosphates is not established yet. Biochemical syntheses of ppGpp and pppGpp are possible using *E. coli* ribosome, ATP and GDP or GTP, but this method is not suitable for industrial production of large amounts, because of the complicated processes and extremely low yield. Other new nucleoside 5'-phosphate (mono, di or tri) 3' (2')-diphosphates such as pppApp, ppApp, pppIpp, etc. cannot be produced by *E. coli.* In order to investigate profoundly the physiological role of these nucleotides in organisms, development of an economical and simple method for their preparation has been awaited. ATP is the most important substance in phosphorylation and energy metabolism of organisms, and recently it was shown that *E. coli* and *B. subtilis* can synthesis enzymatically the characteristic nucleotides, ppGpp and pppGpp, which participate in nucleic acid and protein syntheses, from ATP and GDP or GTP. However, the purification of the enzyme playing a part in the formation of ppGpp and pppGpp has been unsuccessful so far. A number of phosphotransferases and nucleotide-degrading enzymes have been isolated from microorganisms and characterized, but the enzyme concerned with the formation of the aforementioned nucleoside phosphates has not been reported yet.

SUMMARY OF THE INVENTION

We have aimed toward the use of purine nucleoside phosphate compounds as biochemical reagents, high energy phosphate additives and medicines, and have continued to search through a wide variety of natural sources for microorganisms possessing a potential nucleotide pyrophosphotransferase activity. As a result of screening, a new species belonging to Streptomyces, *Streptomyces adephospholyticus* nov. sp. A4668, which possesses a potential nucleotide pyrophosphotransferase activity was isolated, and the enzyme which produces pppGpp, ppApp, pppIpp, etc. by catalyzing the transfer of pyrophosphoryl group from ATP, dATP and pppApp to ATP, GTP, GDP, IDP, AMP, etc. was purified to a substantially homogeneous entity from the culture filtrate. Furthermore, the present inventors discovered the occurrence of nucleotide pyrophosphotransferase in several known species of actinomycetes, and succeeded in readily producing the nucleoside 5'-phosphate (mono, di or tri) 3' (2')-diphosphates by means of the characteristic transfer of pyrophosphoryl group at the 5'-position of ATP, dATP and pppApp to purine nucleoside phosphates such as AMP, ADP, ATP, GMP, GDP, IDP, ITP, etc. using the cultured broth and mycelium of nucleotide pyrophosphotransferase — producing microorganisms. In addition, the present invention provides a method for the preparation and characterization of the enzyme.

Herein

AMP is adenosine 5'-monophosphate
ADP is adenosine 5'-diphosphate
GMP is guanosine 5'-monophosphate
IMP is inosine 5'-monophosphate
IDP is inosine 5'-diphosphate
ITP is inosine 5'-triphosphate
p(CH$_2$)ppA is β,γ-methylene adenosine 5'-triphosphate
p(CH$_2$)ppG is β,γ-methylene guanosine 5'-triphosphate
ppApp is adenosine 5'-diphosphate 3' (2')-diphosphate Furthermore, from the results of extensive studies on the physiological role of nucleotides in organisms and the distribution and biochemistry of the enzyme, the present inventors found that the nucleotide pyrophosphotransferase stimulates or inhibits the growth of various tumor cells in culture and also exhibits potent antitumor activity. Furthermore, the new nucleotide 5'-phosphate (mono, di or tri) 3' (2')-diphosphates inhibit the growth of leukemic L1210 cells in mice and prevent thrombus formation.

The present invention was achieved on the basis of discoveries of medical uses such as chemotherapeutic and diagnostic agent of these nucleotides.

It is an object of the present invention to provide new nucleoside 5'-phosphate (mono, di or tri) 3' (2')-diphosphates and their salts expressed as the following general formula:

mXpp

It is another object to provide a method for producing new nucleoside 5'-phosphate (mono, di or tri) 3' (2')-diphosphates as described above by the enzymatic transfer of a pyrophosphoryl group from specified nucleotides to other specified nucleotides using microorganisms or an enzyme therefrom. It is a further object to provide new nucleoside 5'-phosphate (mono, di or tri) 3' (2')-monophosphates lacking one phosphate at the 3' (2')-position of the above described nucleoside 5'-phosphate (mono, di or tri) 3' (2')-diphosphates. It is a still further object to provide a new nucleotide pyrophosphotransferase characteristically catalyzing the pyrophosphoryl transfer reaction.

Still another object is the provision of a process for making the characteristic nucleotide pyrophosphotransferase using microorganisms. Other objects are to provide a chemotherapeutic agent for cancer and one for the use in inhibiting or preventing thrombus formation in, for example, postoperative situations and conditions where platelet adhesion is excessive. This will be evident from the following detailed discussion of our invention.

BRIEF EXPLANATION OF THE DRAWINGS

FIGS. 4 and 5 are NMR spectra of guanosine 5'-diphosphate 3'-diphosphate and inosine 5'-triphosphate 3'-diphosphate respectively.

FIG. 6 is $^{13}C$ NMR spectrum of adenosine 5'-triphosphate 3'-diphosphate in $D_2O$ (100 MHz).

FIG. 8 shows the relationship of enzyme concentration and thermal stability of the enzyme obtained from *Streptomyces morookaensis* ATC 19166, in which vertical axis represents % of residual activity.

DETAILED EXPLANATION OF THE INVENTION

Figure 1:
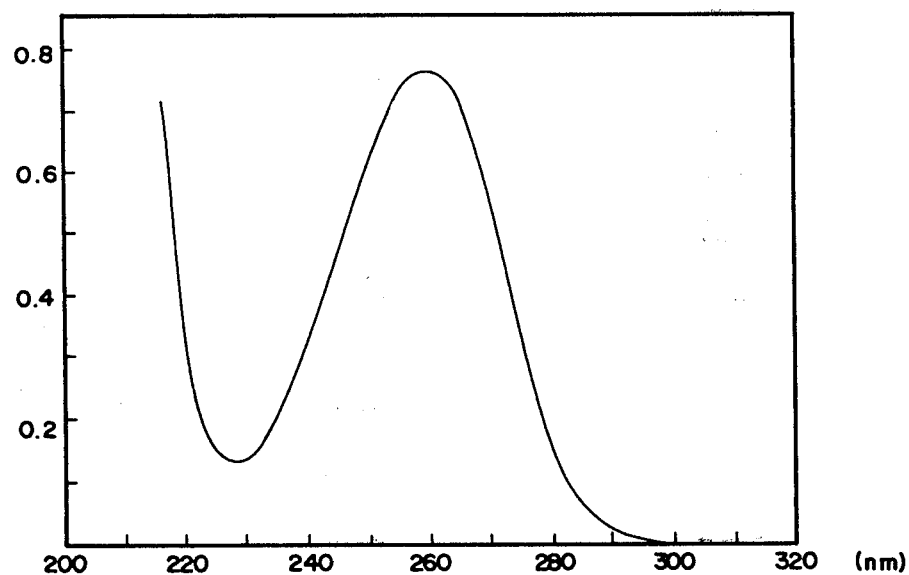
FIGS. 1 to 3 respectively show ultraviolet absorption spectra of adenosine 5'-triphosphate 3'-diphosphate, guanosine 5'-diphosphate 3'-diphosphate and inosine 5'-triphosphate 3'-diphosphate in $H_2O$, in which the vertical axis represents optical density.
Figure 2:
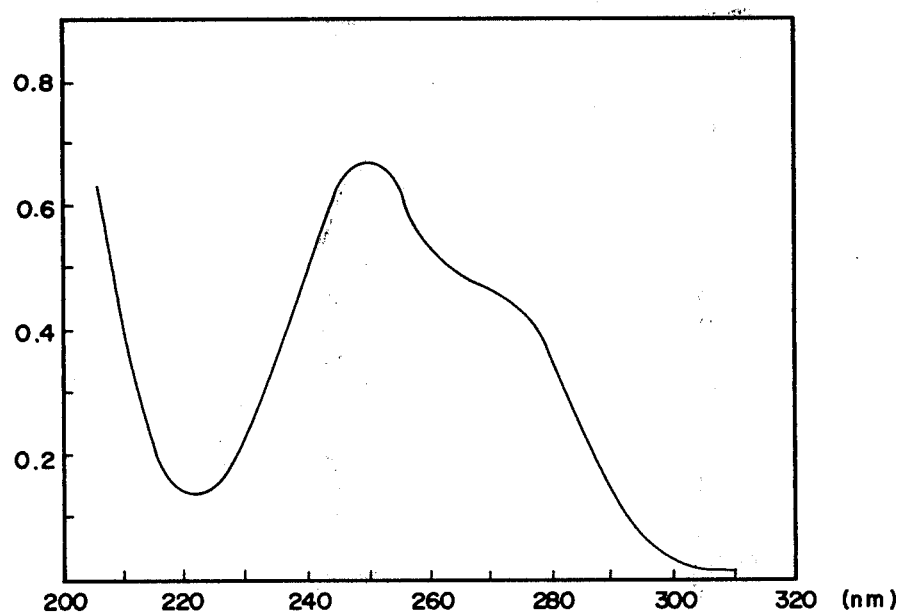
Figure 3:
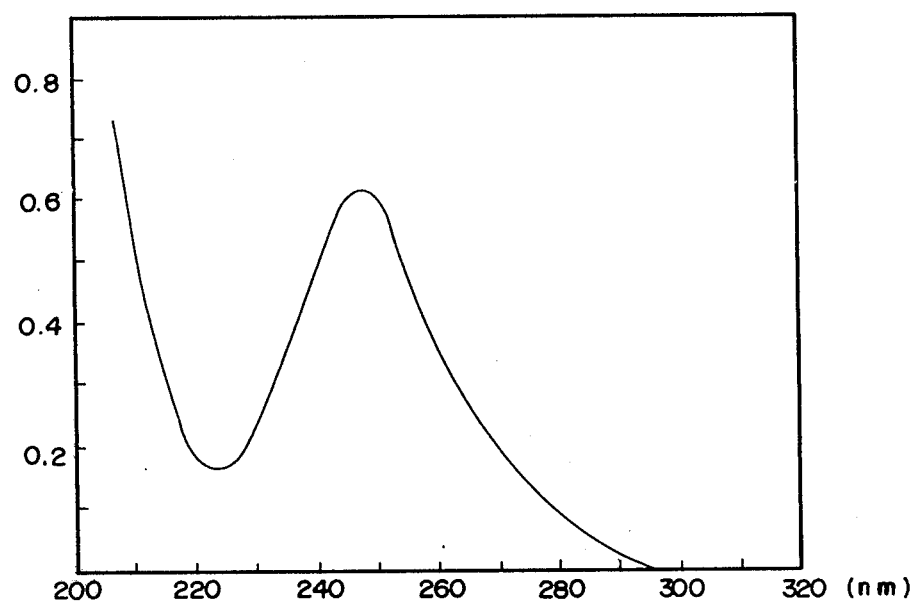
Figure 4:
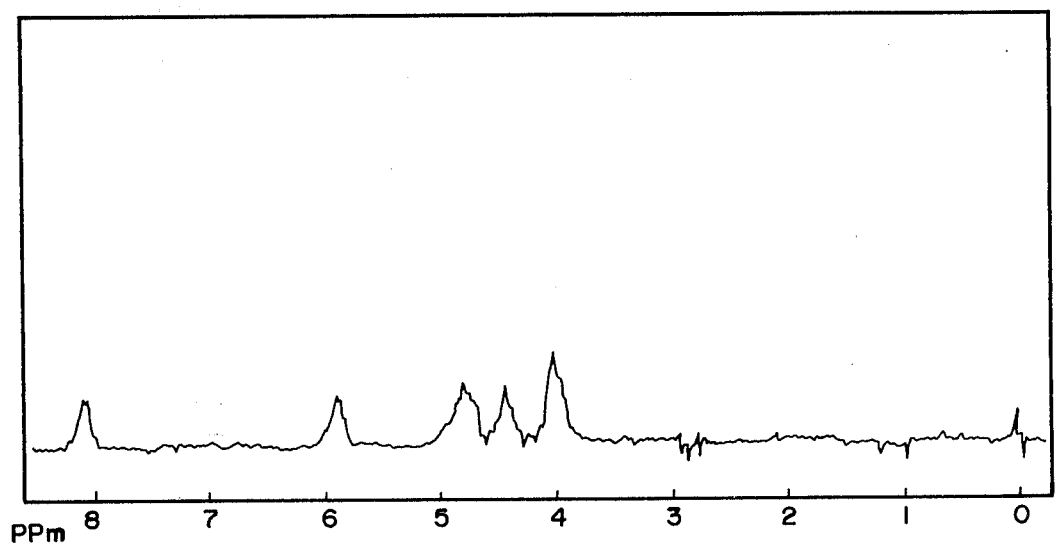

Microorganisms and the methods for their cultivation

Microorganisms:

The microorganisms used in the present invention are a new species of Streptomyces, *Streptomyces adephospholyticus*, nov. sp. A4668 and known species of actinomycetes belonging to the genera Streptomyces, Actinomyces and Streptoverticillium. Since the actinomycetes are easily mutable naturally or artifically, the microorganisms in the present invention include the typical strain and all the natural and artificial variants and mutants thereof. That is, the microorganisms of the present invention include all strains of actinomycetes possessing nucleotide pyrophosphotransferase activity.

The following strains are cited as examples:
*Streptomyces aspergilloides* ATCC 14804
*Streptomyces morookaensis* ATCC 19166
*Streptomyces hachijoensis* ATCC 19769
*Streptoverticillium septatum* ATCC 27464
*Actinomyces violascens* ATCC 23968

The cultures of these strains have been deposited in the American Type Culture Collection, Rockville, Md., and anyone can obtain the strains under the prescribed procedures.

One of the strains used in the present invention, *Streptomyces adephospholyticus* nov. sp. A4668 was newly isolated from a soil sample collected at Sakai-city, Osaka, Japan, and shows the following morphological, macroscopic, microscopic and biochemical properties:

(a) Morphological characteristics (Incubated on a malt yeast extract agar medium at 28° C. for 10 to 20 days).

Aerial mycelia were simply branched, and at the tips of hyphae sporophores formed long open spirals. Mature spore chain was long and bore more than 10 spores per chain.

Spores were oval with spiny surface, and measured 0.4–0.6 × 0.6–0.8μ and the presence of flagella, sporangia or sclerotia was not observed.

Incubation was carried out at 28° C. unless otherwise specified.

(b) Cultural characteristics on various media:
  (1) On sucrose — nitrate agar:
    Growth: slow or moderate
    Aerial mycelium: Partly velvety, white with a purplish tinge
    Substrate mycelium: White to pale yellow, partly pale yellow-orange
    Soluble pigment: none
  (2) On glucose-asparagine agar:
    Growth: moderate and wrinkled
    Aerial mycelium: partly velvety, white with a purplish tinge
    Substrate mycelium: light yellow
    Soluble pigment: none
  (3) On glycerin — asparagine agar:
    Growth: moderate
    Aerial mycelium: partly velvety, at first a white with pink, after two weeks of cultivation a light grayish-purple
    Substrate mycelium: at first a light yellow orange, later a light gray reddish-brown
    Soluble pigment: usually none, sometimes a pale yellow after two weeks of cultivation
  (4) On starch agar (starch-inorganic salts agar):

Growth: moderate
Aerial mycelium: partly pointed, white to grayish purple or purple or purplish white on old culture.
Substrate mycelium: white to pale yellow in young culture, light yellow-orange in old culture.
Soluble pigment: none
(5) On tyrosine agar:
Growth: moderate
Aerial mycelium: abundant, white, very light purple in old culture
Substrate mycelium: grayish yellow to rose beige or moderate yellowish pink, light brown in old culture
Soluble pigment: yellow to grayish yellow-brown, disappeared in old culture
(6) On nutrient agar:
Growth, moderate, surface wrinkled
Aerial mycelium: none
Substrate mycelium: light gray reddish brown
Soluble pigment: light brown which disappeared in old culture
(7) On yeast extract-malt extract agar:
Growth: abundant, wrinkled
Aerial mycelium: velvety, white to pale yellow
Substrate mycelium: pale yellow to grayish yellow, moderate yellowish pink to light gray reddish brown in old culture
Soluble pigment: none
(8) On oat meal agar:
Growth: abundant, wrinkled
Aerial mycelium: white, changing to grayish yellowish pink or purplish pink in old culture
Substrate mycelium: grayish yellow in young culture, light grayish yellow-brown to light brown in old culture
Soluble pigment: none
(c) Physiological characteristics:
(1) Growth temperature:
Optimal temperature is 25° C. to 30° C., and scant growth at 10° C., but no growth above 37° C.
(2) Gelatin liquefaction on glucose-peptone-gelatin medium at 20° C.: positive
(3) Starch hydrolysis on starch-inorganic salts agar: positive
(4) Peptonization and coagulation of skimmed milk: positive
(5) Melanin formation on tyrosine agar, peptone yeast extract $Fe^{++}$ agar, and tryptone yeast extract broth: positive
(6) Nitrate reduction: positive
(7) Utilization of carbohydrates on Pridham-Gottlieb basal medium:
Abundant growth with L-arabinose, D-xylose, D-glucose, D-fructose, inositol, raffinose and D-mannitol; slight growth with sucrose; no growth or very slight growth with L-rhamnose Classifying on the basis of the morphological and physiological characteristics of the strain according to "The Actinomycetes", Vol. II, 1961, by S. A. Waksman, Bergey's Manual of Determinative Bacteriology, 7th edition, 1957, and International Journal of Systematic Bacteriology, Vol. 18 (1968) No. 2 and 4, and Vol. 19 (1969) No. 4, the strain belongs to the genus Streptomyces, because vegetative mycelia were not segregated into bacillary fragments in the liquid media and aerial mycelia were simply branched with the sporophores forming long open spirals at the tips of hyphae.

Comparing these microbiological characteristics with those of known species of Streptomyces, the present strain apparently resembles the Lavendulae series, *Streptomyces lavendulae* and *St. venezualae* but is different from those strains in detail.

Among known species, the cultural and physiological characteristics of the present strains were very similar to *Actinomyces violascens*. From the results of parallel cultures of the present strain and the standard strain of *Act. violascens* ISP 5183, some differences were found in the cultural characteristics such as the color of aerial and substrate mycelia and appearances on yeast extract malt extract agar, tyrosine agar, peptone-yeast extract-$Fe^{++}$ agar, nutrient agar media, and also in the carbon assimilation patterns. The present strain could assimilate D-mannitol, inositol and fructose, but *Act. violascens* could not assimilate D-mannitol and only weakly was able to utilize the other two sugars.

From the results mentioned above, the present strain was identified as a new species and named *St. adephospholyticus* nov. sp. A 4668.

A culture of *St. adephospholyticus* A 4668 was deposited in the Fermentation Research Institute, Japan, on 24, March, 1973, and in the American Type Culture Collection, Rockville, Md., and added to its permanent collection of microorganisms at ATCC No. 31122 and FERM No. 1992, respectively.

Cultivation of the microorganisms possessing nucleotide pyrophosphotransferase activity:

The new species, *St. adephospholyticus*, and other authentic strains of actinomycetes possessing nucleotide pyrophosphotransferase activity include the enzyme constitutively, and are characterized by the fact that they excrete the enzyme in the culture filtrate extracellurally under the general fermentation conditions used for the cultivation of other actinomycetes. Although cultivation on a solid medium and recovery from mycelium are possible in the preparation of the enzyme, recovering the enzyme which has been actively excreted in the culture filtrate by the submerged aerobic culture is especially advantageous industrially in the production of large quantities of the pure enzyme preparation.

Media consisting of known kinds of nutritional sources for the growth of actinomycetes can be used for the production of nucleotide pyrophosphotransferase. As the source of carbon, the medium preferably contains glucose, sucrose, maltose, fructose, starch, starch hydrolysate, glycerol, glycine, alanine, glutamic acid, molasses, dextrin, oil, fats and the like; as the source of nitrogen, the medium preferably contains organic materials such as peptone, meat extract, yeast extract, soybean meal, fish meal, casein hydrolysate and urea, and inorganic sources of nitrogen such as nitrates and ammonium salts, e.g. ammonium sulfate and ammonium chloride; and the medium also contains other inorganic salts such as sodium chloride, potassium chloride, potassium phopshate, magnesium sulfate, and calcium carbonate and trace amounts of heavy metals such as mangenese, iron, zinc and the like. In aerated submerged cultures, an antifoam such as liquid paraffin, soybean oil, fatty oils or silicone is used.

The culturing temperature is usually 20° C. to 40° C., with the preferred range of temperature being 25° to 30° C. It is not necessary to control the pH of the culture medium during the cultivation; the enzyme activity in the culture filtrate reaches a maxiumum at 42 to 72 hours of incubation.

Enzyme and method of purification thereof:

Purification:

An example for the production of the enzyme is described below.

Figure 7:
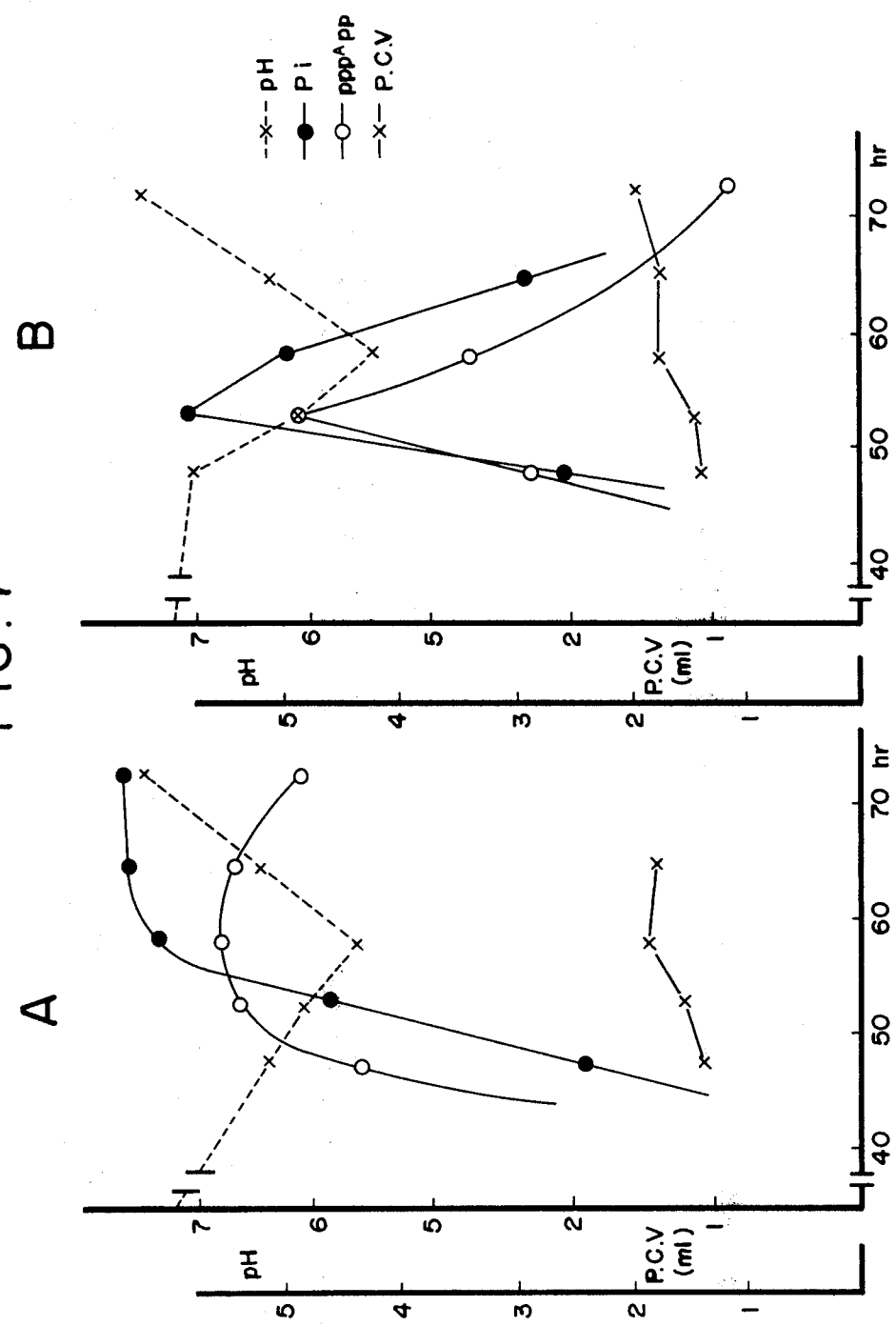
FIG. 7 shows the time course of enzyme production by (A) *Streptomyces morookaensis* ATCC 19166 and (B) *Streptomyces aspergilloides* ATCC 14808, in which the vertical axis represents ml. of P.C.V. (packed cell volume) and pH (right) and enzyme activity (left) and the horizontal axis represents hours.

A medium (100 ml) consisting of glycerol 2%, polypeptone 4%, $KH_2PO_4$ 0.1%, $K_2HPO_4$ 0.1%, $MgSO_4 \cdot 7H_2O$ 0.04%, $Mn^{++}$ and $Fe^{++}$ 2ppm each was placed in 500 ml Sakaguchi — shaking flasks and sterilized at 120° C. for 15 minutes. To this sterilized medium, *Streptomyces aspergilloides* ATCC 14808 and *St. morookaensis* ATCC 19166 were inoculated into separate flasks from an agar slant culture by means of a platinum loop, and incubated on a reciprocal shaker at 28° C. The time course of the enzyme production in the culture filtrate, as shown in FIG. 7, was determined by the method described later.

FIG. 7A shows the time course of enzyme activity of *St. morookaensis* ATCC 19166 and FIG. 7B is that of *St. aspergilloides* ATCC 14808, in which enzyme activity is expressed as units/ml. determined by the formation of pppApp or Pi (inorganic phosphate), and cell growth is expressed as P.C.V. (packed cell volume).

After fermentation, the enzyme can be purified and recovered by conventional methods such as salting-out with ammonium sulfate, solvent precipitation, extraction, adsorption, electrophoresis, electrofocusing, gel-filtration, the use of ion-exchange resins and the like or by a combination of methods where at least one or more are selected from these.

Under cultivation conditions capable of growing microorganisms, the enzyme is found mainly in the liquid part of the culture broth after the mycelia have been removed. Obtaining the enzyme in pure form from the culture filtrate where it has accumulated in high concentration is advantageous from an industrial viewpoint.

Purification and preparation processes of the enzyme from *St. morookaensis* ATCC 19166 is cited as an example in Table 1.

Purity of the final enzyme preparation was examined by polyacrylamide and SDS-polyacrylamide gel electrophoreses, and the purified enzyme preparation migrated as a single band on the gels showing the enzyme to be electrophoretically homogeneous.

The quite low yield of purified enzyme in the example was caused by a considerable loss of enzymatic activity with the removal of impure protein during the purification process and with the rapid inactivation by dilution.

The addition of proteins such as casein and bovine serum albumin and non-ionic surface active agents such as Tween and Span to the enzyme solution protected the enzyme against inactivation, improved the yield of the purified enzyme and made it possible to store the enzyme for a long time.

Enzyme assays were carried out using either of the following methods:

(1) Inorganic phosphate determination by a modification of Nakamura's method: The standard reaction mixture contained 0.25 M glycine-NaOH buffer (pH 10.0), 0.2 ml.; 0.05 M $MgCl_2$, 0.05 ml.; 0.05 M ATP, 0.05 ml.; the enzyme solution (to be diluted by buffer if necessary), 0.1 ml.; and distilled water, 0.1 ml. in a final volume of 0.5 ml. After incubation at 37° C. for 10 minutes, the reaction was terminated by adding 0.5 ml. of 0.2 N acetic acid, and chilling on ice. Immediately, 3 ml. of developing reagent (amidol-molybdate) was added and the mixture was allowed to stand for 10 minutes at 37° C. The optical density was measured at 750 nm and the moles of Pi released were calculated using the standard curve for Pi. A unit of enzyme activity is defined as the amount of enzyme which is capable of forming $1\mu$ mole of Pi per minute under standard conditions.

(2) Determination of pppApp and AMP formed in the reaction mixture using radioactive ATP.

The reaction mixture contained 20 mM adenosine-8-3H-triphosphate (2 mCi/m mole), 5 mM $MgCl_2$, 62.5 mM glycine-NaOH buffer (pH 10.0) and 0.1 ml. of enzyme solution to give a total volume of 0.2 ml. The mixture was incubated at 37° C. for 10 minutes and the incubation was terminated by addition of 0.01 ml. of 1 N acetic acid. Twenty microliters of the reaction mixture were spotted on a polyethyleneimine (PEI) cellulose F thin layer sheet (E. Merck AG), dried and developed in 0.75 M $KH_2PO_4$, pH 3.4, for two hours at room temperature. After chromatography the sheets were dried and exposed to ultraviolet light provided by a Manasul UV lamp to localize the pppApp and AMP formed. The spots on the chromatograms corresponding to pppApp and AMP were cut out and placed in a scintillation vial containing 0.5 ml. of 0.1 N HCl. Vials were boiled for 15 minutes to elute nucleotides adsorbed on the PEI-cellulose and radioactivity was measured by 10 ml. of BRAY Solution in a liquid scintillation counter. A unit of enzyme activity is defined as the amount of enzyme Table 1

| Processes | Volume (ml) | Total activity (units) | Total protein ($OD_{280nm}$) | Specific activity | Yield (%) |
|---|---|---|---|---|---|
| Culture filtrate | 20000 | 77190 | 1218420 | 0.63 | 100 |
| $(NH_4)_2SO_4$ ppt. 60% saturation | 9789 | 471811 | 256220 | 1.84 | 61.1 |
| DEAE-cellulose column (pH 5.6) | 11200 | 436800 | 146940 | 2.98 | 56.6 |
| CM-Sephadex C-50 column (pH 5.6) | 1660 | 72422 | 16384 | 4.42 | 9.4 |
| CM-Sephadex C-25 column (pH 5.5) | 910 | 16244 | 309 | 52.6 | 2.1 |
| DEAE-Sephadex A-25 (pH 8.7) | 159 | 6298 | 20 | 315 | 0.8 |
| Sephadex G-75 (pH 8.7) | 14 | 6019 | 6.7 | 903 | 0.8 |

Purification processes of nucleotide pyrophosphotransferase from *Streptomyces morookaensis* ATCC 19166 forming 1μ mole of pppApp or AMP per minute under the above condition.

Enzyme:

The nucleotide pyrophosphotransferase preparation obtained from the microorganisms described in the present invention by a combination of the various above-mentioned methods was demonstrated to be a new enzyme possessing the following physicochemical properties;

(a) Enzyme reaction and substrate specificity:

The enzymes obtained from the above-mentioned six microorganisms catalyze the transfer reaction of a pyrophosphoryl group from ATP, dATP and pppApp to 3' (2')-position of AMP, ADP, ATP, GMP, GDP, GTP, IMP, IDP, ITP, p(CH$_2$)ppA, p(CH$_2$)ppG and the like. The new reaction products are pApp, ppApp, pppApp, pGpp, ppGpp, pppGpp, pIpp, ppIpp, pppIpp, p(CH$_2$)ppApp, p(CH$_2$)ppGpp and the like.

Other pyrimidine nucleotides, paranitrophenylphosphate, pyrophosphate, glucose-1-phosphate, glycerin-3-phosphate, tripolyphosphate, nucleosides, and bases cannot accept or donate phosphoryl group. There are some differences in pyrophosphate acceptor and donor activities depending upon pH, metal ions and microorganisms, but generally the preference of phosphate donor activity is in the order of ATP, pppApp and dATP, and that of phosphate acceptor activity is in the order of adenosine phosphate, guanosine phosphate and inosine phosphate.

(b) pH optimum and metal requirements:

The enzyme capable of catalyzing the formation of pppApp from ATP exhibited an absolute requirement for divalent metal ions, and no activity in the reaction mixture is detected in the absence of divalent metal ions. The pH optimum and optimal concentrations of divalent ions depend upon specific metal ions and enzyme sources as shown in Table 2.

(c) Optimal temperature:

There is no difference in the optimal temperature of the enzyme reaction irrespective of the kind of microorganisms employed. The temperature of 40° to 45° C. is optimal under optimal pH in the presence of magnesium ion.

(d) Stability

Enzyme isolated from six strains of actinomycetes are similarly stable at a pH ranging from 7 to 11 and unstable at an acidic pH below 6. When the enzyme solution has stood at 37° C. for two hours, residual activity is 10 to 20% at pH 4, 30 to 50% at pH 5, and 60 to 70% at pH 6. Although thermal stability is influenced by the degree of dilution of the enzyme solution and the presence of impure protein, generally the enzyme is unstable above 60° C. For example, when purified enzyme obtained from St. morookaensis ATCC 19166 is diluted to various concentrations of enzyme protein and heated for 10 minutes in 0.05 M glycine-NaOH buffer (pH 10) containing 5 × 10$^{-3}$ M magnesium ion, thermal inactivation cannot be observed even at 90° C. when the concentration of enzyme protein is high, but at a low concentration of enzyme protein, rapid inactivation occurs even at 30° C. as shown in FIG. 8.

Thermal inactivation and inactivation at acidic pH can be prevented by the addition of 20 to 300 μg/ml. of proteins such as serum albumin, casein and the like, or 0.001 to 0.01% of non-ionic surface active agents such as Tween, Span and the like.

(e) Inhibitors:

Inhibitory actions of 40 substances which are general enzyme inhibitors such as nucleosides, nucleotides and their bases were examined for their effect on the enzymes obtained from the six actinomycetes.

Among the non-substrate nucleic acids tested, guanine, guanosine, d-GDP, and d-GTP (10 mM each) produced marked inhibition, while other nucleic acids such as adenine, adenosine, 2' (3') AMP, hypoxanthine, inosine, xanthine, uracil, uridine, cytosine, cytidine, CMP and NAD were not inhibitory. Concentrations of sodium borate, 5 mM mercuric acetate, 5 mM iodoacetate and 0.1 mM N-bromosuccinimide inhibit 50 to 80% of enzyme activity.

Table 2

| Relationship between pH and metal ions on the enzyme activity | | | | |
|---|---|---|---|---|
| Enzyme sources | Metal ions | Optimum concentration (M) | Optimum pH | Relative activity (%) |
| Actinomyces violascens ATCC 23968 | Mg$^{++}$ | 5 × 10$^{-3}$ | 10 – 10.5 | 100 |
| | Mn$^{++}$ | 3 × 10$^{-3}$ | 9.5 – 10 | 45 |
| | Co$^{++}$ | 5 × 10$^{-3}$ | 9 | 43 |
| | Zn$^{++}$ | 5 × 10$^{-3}$ | 9.5 | 15 |
| | Fe$^{++}$ | 5 × 10$^{-3}$ | 9 | 30 |
| Streptoverticillum septatum ATCC 27464 | Mg$^{++}$ | 10$^{-2}$5 × 10$^{-3}$ | 9.5 – 10 | 100 |
| | Mn$^{++}$ | 10$^{-2}$ | 10 – 10.5 | 40 |
| | Co$^{++}$ | 7 × 10$^{-3}$ | 8 – 8.5 | 35 |
| | Zn$^{++}$ | 5 × 10$^{-3}$ | 8.5 – 9 | 20 |
| | Fe$^{++}$ | 5 × 10$^{-3}$ | 7.5 – 8 | 20 |
| Streptomyces morookaensis ATCC 19166 | Mg$^{++}$ | 10$^{-2}$5 × 10$^{-3}$ | 10 – 11 | 100 |
| | Mn$^{++}$ | 3 × 10$^{-3}$ | 11 | 60 |
| | Co$^{++}$ | 7 × 10$^{-3}$ | 9 – 9.5 | 65 |
| | Zn$^{++}$ | 5 × 10$^{-3}$ | 9.5 | 15 |
| | Fe$^{++}$ | 5 × 10$^{-3}$ | 8 – 9 | 25 |
| Streptomyces aspergilloides ATCC 14808 | Mg$^{++}$ | 5 × 10$^{-3}$ | 10 – 11 | 100 |
| | Mn$^{++}$ | 7 × 10$^{-3}$ | 10.5 | 50 |
| | Co$^{++}$ | 7 × 10$^{-3}$ | 8.5 – 9 | 60 |
| | Zn$^{++}$ | 5 × 10$^{-3}$ | 9 – 10 | 20 |
| | Fe$^{++}$ | 5 × 10$^{-3}$ | 8.5 | 55 |
| Streptomyces hachjioensis ATCC 19769 | Mg$^{++}$ | 10$^{-2}$5 × 10$^{-3}$ | 9.5 | 100 |
| | Mn$^{++}$ | 5 × 10$^{-3}$ | 9 – 9.5 | 35 |
| | Co$^{++}$ | 7 × 10$^{-3}$ | 8 – 8.5 | 75 |
| | Zn$^{++}$ | 2 × 10$^{-3}$ | 8.5 – 9 | 20 |
| | Fe$^{++}$ | 5 × 10$^{-3}$ | 7.5 | 25 |

(f) Stimulation:

Enzyme activity can be markedly stimulated, that is, increased by the addition of 0.05 to 0.001% of non-ionic surface active agents such as Tween 20, 40 and 60, and Span 20, 40, 60 and 80 and the like, 0.005-0.001% of sodium dodecyl sulfate, 0.001 to 0.01% of polyethylene glycol 6000, 10 to 200 µg/ml. of proteins such as serum albumin and casein and the like. Enzyme activity is further increased by preincubating the enzyme with these activators at 30° to 0° C. for 10 to 60 minutes prior to enzyme reaction.

(g) Enzyme assay:

As described above.

Figure 9:
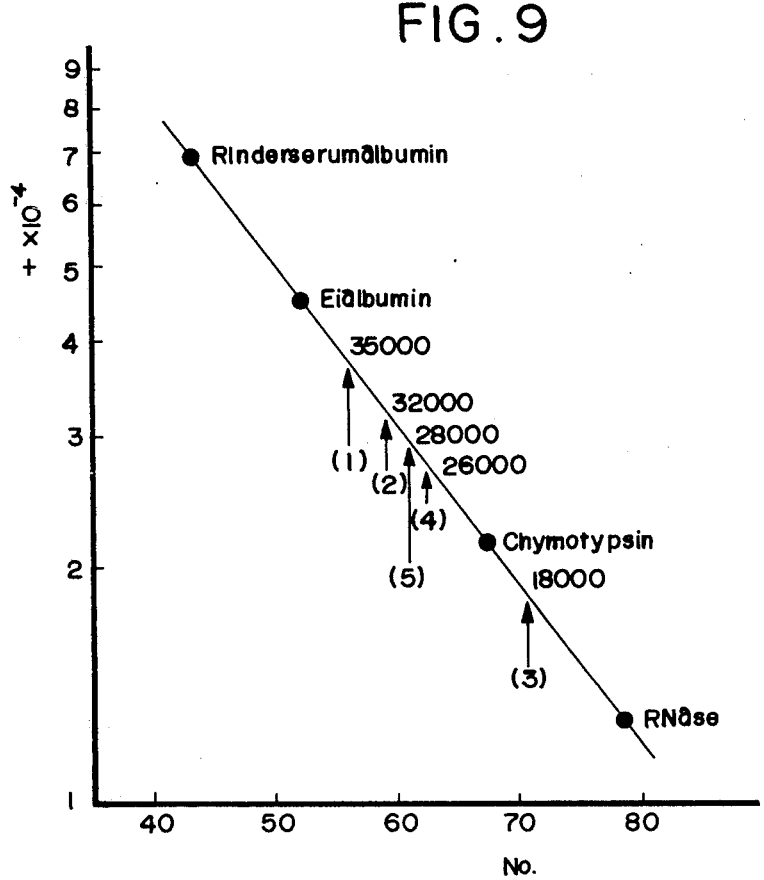
FIG. 9 shows the molecular weight of the enzymes obtained from the microorganisms according to this invention, calculated by using Sephadex G-75 gel filtration and standard proteins as controls in which the vertical axis represents molecular weight ($X\ 10^4$) and the horizontal axis represents the fraction number.

(h) Molecular weight:

When the purified enzymes isolated from each strain of actinomycetes are applied to calibrated columns of Sephadex G-75 which has been equilibrated with 0.05 M glycine-NaOH buffer, pH 9.0, the enzyme activity is eluted as a single symmetrical peak and the apparent molecular weight of the enzyme is calculated employing reference proteins, namely chymotrypsin, ovoalbumin, RNase and calf serum albumin, as shown in FIG. 9. In FIG. 9, (1) shows the molecular weight of *St. morookaensis* ATCC 19166 enzyme, (2) is the molecular weight of *St. aspergilloides* ATCC 14808 and *Streptoverticillium septatum* ATCC 27464, (3) is the molecular weight of *St. hachijoensis* ATCC 19769, (4) is the molecular weight of *Actinomyces violascens* ATCC 23968 and (5) is the molecular weight of *St. adephospholyticus* A 4668. ATCC 31122.

If gel-filtration is carried out in a solution of high ionic strength (0.1 M KCl), the apparent molecular weight becomes small as shown in parentheses in Table 3. Molecular weights of the enzymes are summarized in Table 3, which also shows the results of gel-filtration and the results obtained in polyacrylamide gel electrophoresis in 0.1% SDS using calf serum albumin, lysozyme and γ-globulin as references.

Table 3

| Strains | Methods Sephadex G-75 Gel filtration | SDS-polyacrylamide electrophoresis |
| --- | --- | --- |
| *Actinomyces violascens* ATCC 23968 | 26000 | — |
| *Streptomyces morookaensis* ATCC 19166 | 35000(25000) | 23000 – 24000 |
| *Streptomyces aspergilloides* ATCC 14808 | 32000(23000) | 21000 – 23000 |
| *Streptoverticillium septatum* ATCC 27464 | 32000 | — |
| *Streptomyces hachijoensis* ATCC 19769 | 18000 | — |
| *Streptomyces adephospholiticus* ATCC 31122 | 28000 – 29000 | — |

(i) Sedimentation coefficient:

Using a glycerol gradient (15-55%) centrifugation employing γ-globulin, calf serum albumin and RNase as internal standards gave sedimentation coefficients of 2.65 for *St. morookaensis* ATCC 19166 enzyme, 2.45 for *St. aspergilloides* ATCC 14808 enzyme, and 2.10 for *St. adephospholyticus* enzyme.

(j) Isoelectric point:

Isoelectric points of the purified enzymes were determined using an electrofocusing column with an Ampholine of pH 5 to 8 (LKB Instruments Inc.), as shown in Table 4.

Table 4

| Strains | Isoelectric point pH |
| --- | --- |
| *Actinomyces violascens* ATCC 23968 | 7.5 |
| *Streptomyces morookaensis* ATCC 19166 | 6.9 |
| *Streptomyces aspergilloides* ATCC 14808 | 6.8 |
| *Streptoverticillium septatum* ATCC 27464 | 9.2 |
| *Streptomyces hachijoensis* ATCC 19769 | 8.3 |
| *Streptomyces adephospholyticus* ATCC 31122 | 7.6 |

As described above, the physico-chemical properties of the enzyme do not coincide with those of known enzymes, and the enzymes are confirmed as a new and characteristic type of enzyme.

A process for the production of nucleotide pyrophosphotransferase is characterized by cultivating microorganisms belonging to the genera Streptomyces, Streptoverticillium and Actinomyces according to conventional methods, and recovering the enzyme from culture filtrate and mycelia during the refining processes using ammonium sulfate precipitation, solvent precipitation, extraction, chromatography employing ion-exchange resin, and gel filtration. Moreover, there is provided an enzymatic method for easily producing the new nucleoside 5'-phosphate (moni, di or tri) 3' (2')-diphosphates with high yields by the transfer of pyrophosphoryl group from the 5'-position of ATP, dATP and pppApp to the 3'-position of guanosine, adenosine or inosine nucleoside phosphates (mono, di or tri).

Production of the new nucleoside 5'-phosphate (mono, di or tri) 3' (2')-diphosphates:

Various enzyme preparations such as cultured broth, culture filtrate, cell homogenate, $(NH_4)_2SO_4$ ppt, fractions from ion exchange resin chromatography and gel filtration and the like containing nucleotide pyrophosphotransferase can be used for the production of the new nucleoside 5'-phosphate (mono, di or tri) 3' (2')-diphosphates in the present invention.

The phosphate donors are limited to ATP, dATP and pppApp and phosphate acceptors are ATP, ADP, AMP, GTP, GDP, GMP, ITP, IDP, IMP and the like, corresponding to the new nucleoside 5'-phosphate 3' (2')-diphosphate formed. One or more phosphate donors and one or more phosphate acceptors can be provided for the enzyme reaction.

An example of the composition of the reaction mixture is given as follows:

| | |
| --- | --- |
| 250 mM glycine-NaOH buffer (pH 10.0) | 6 ml. |
| 50 mM ATP sodium salt | 4 ml. |
| 50 mM phosphate acceptor (nucleoside phosphate) | 4 ml. |
| 50 mM $MgCl_2$ | 4 ml. |
| 3 units/ml. enzyme solution | 6 ml. |
| Total | 24 ml. | in which the phosphate donor and acceptor can be a free acid or sodium, lithium, and potassium salts thereof, or a combination of free acid and salts, and the ratio of the phosphate donor to the acceptor can be altered depending upon reaction conditions and enzyme activity.

It is preferred that the enzymatic reaction is carried out under optimal conditions of pH, temperature, present or absence of divalent metal ions, appropriate substrate concentration and the like whereby the enzyme has been shown to reach maximum activity. For example, the optimal range of pH is from 6 to 11, the optimal temperature range is from 25° to 40° C. and the divalent metal ions employed are $Fe^{++}$, $Mn^{++}$, $Mg^{++}$, $Co^{++}$, $Zn^{++}$ and the like. Generally the enzyme reaction is carried out at 37° C. for 2 to 4 hours.

After termination of the enzyme reaction, the reaction mixture is neutralized with 0.1 N hydrochloric acid, and the new purine nucleoside 5'-phosphate (mono, di or tri) 3' (2')-diphosphates are isolated and purified by a combination of conventional refining methods such as adsorption on active carbon, chromatography by anion or cation ion-exchange resins, solvent precipitation and the like. For example, the reaction mixture as described above is incubated at 37° C. for 4 hours, neutralized with 0.1 N HCl and applied to an ion exchange resin column (Dowex-1, Cl type, DEAE-Sephadex A25). Adsorbed reaction products were eluted with a proper buffer (diluted HCl or diluted HCl + NaCl for Dowex 1, Cl type to prepare sodium salt, and Tris-HCl+LiCl for DEAE-Sephadex to prepare lithium salt), and the eluate was adsorbed on active carbon and eluted again with ammonia alcohol (50% ethanol-1.4% ammonia water, ammonia-acetone or 2.8% ammonia water).

After the excess ammonia in the eluate was removed by concentration in vacuo, the sodium or lithium salts of the new nucleoside 5'-phosphate 3' (2')-phosphates were obtained as a white microcyrstalline powder by allowing the solution to stand in the cold, or by the addition of solvents such as alcohols, acetone and the like. To prepare the free acid, the sodium or lithium salt of the nucleoside 5'-phosphate 3' (2')-phosphate is dissolved in acidic water and adsorbed on active carbon. Then the free acid is eluted with ammonia alcohol (50% ethanol-1.4% ammonia water) and after the excess ammonia is removed by evaporation in vacuo, the free acid is precipitated with 10 volumes of acetone.

The structure of the new nucleoside phosphate:

The structures of the new nucleoside 5'-phosphate 3' (2')-phosphate in the present invention are elucidated by UV adsorption spectrum, total phosphate determination, NMR analysis, and enzymatic degradation as follows:

For example, when the reaction mixture in which ATP was incubated with the enzymes in the presence of $Mg^{++}$ is subjected to and adsorbed on an ion-exchange DEAE-Sephadex A-25 column ($Cl^-$), and eluted with a buffer where the lithium chloride concentration is increased from 0.1 to 0.3 M lineally, two peaks at $OD_{260nm}$ are eluted by 0.1 M and 0.2 M lithium chloride. These fractions are pooled and concentrated in vacuo, and then two kinds of nucleotides are precipitated by the addition of 10 volumes of 95% ethanol. From the results of periodate oxidation, total phosphate determination, ultra violet spectrum, $^{13}$C-NMR analysis and enzymatic degradation by snake venom dephosphodiesterase and 3'-nucleotidase, the first peak was determined to be AMP lithium salt and the second peak was confirmed to be a new adenosine 5'-triphosphate 3' (2')-diphosphate lithium salt, which has a pyrophosphate structure attached to the 3' (2')-position of ATI as follows (I):

Structure of pppApp

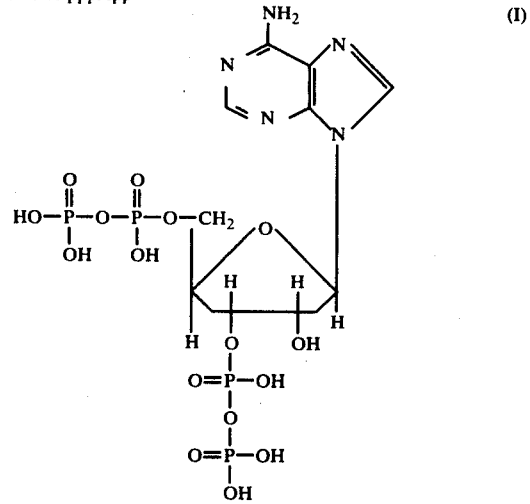

To characterize and identify the new nucleoside 5'-phosphate (mono, di or tri) 3' (2')-diphosphates produced by the methods of the present invention, the results of lithium content, spectral properties of UV and NMR, and molar ratio of Pi and nucleotide calculated by the values of total phosphate and ribose contents are summarized in Table 5. Further, UV adsorption and NMR spectra of typical nucleoside 5'-phosphate (mono, di or tri) 3' (2')-diphosphates according to the present invention are shown in FIGS. 1 to 6 to clarify the characteristics of these compounds.

Table 5

| Properties | Nucleoside 5'-phosphate 3'-diphosphate lithium salt | | | | | |
|---|---|---|---|---|---|---|
| | pppApp | ppApp | pppGpp | ppGpp | pGpp | ppplpp |
| Ultraviolet adsorption (Remarks 1) | | | | | | |
| λmax (1) | 258 | 258 | 258 | 258 | 257.5 | 250 |
| (2) | 260.5 | 260 | 254.5 | 254.5 | 253.5 | 249.5 |
| (3) | 260.5 | 260 | 258 | 258 | 258 | 254.5 |
| λmin (1) | 230.5 | 230.5 | 229 | 229 | 229 | 221.5 |
| (2) | 228 | 228 | 224 | 224 | 223.5 | 223 |
| (3) | 228 | 228 | 226 | 225.5 | 225.5 | 225 |
| ε260nm $10^{-3}$ | | | | | | |
| (1) | 14.3 | 14.2 | 11.8 | 11.8 | 11.8 | 7.4 |
| (2) | 15.1 | 15.0 | 12.0 | 11.9 | 12.1 | 7.4 |
| (3) | 15.1 | 15.0 | 11.8 | 11.8 | 11.8 | 12.2 |
| Phosphate content (molar ratio) | 1:4.92 | 1:4.00 | 1:4.95 | 1:3.82 | 1:3.02 | 1:4.69 |
| Lithium content (molar ratio) | 1:7.1 | 1:6.0 | 1:6.8 | 1:6.2 | 1:5.2 | 1:7.2 |
| Binding position of phosphate (Remarks 4) | 5'-, 3'- | 5'- | 5'- | 5'- | 5'- | 5'- |

Table 5-continued

| Properties | Nucleoside 5'-phosphate 3'-diphosphate lithium salt | | | | | |
|---|---|---|---|---|---|---|
| | pppApp | ppApp | pppGpp | ppGpp | pGpp | pppIpp |
| | 3'- | 3'- | 3'- | 3'- | | 3'- |

Remarks 1: UV absorption was measured in (1) 0.01 N HCl, (2) distilled water and (3) 0.01 N NaOH.

Remarks 2: Total phosphate determination was carried out by Nakamura's method after 0.5 to 3 ml. of sample solution was degraded with 0.5 ml. of 60% perchloric acid, heated for one hour and made up to 10 ml. total volume with distilled water. Inorganic phosphate in a degraded sample was determined from optical density at 700 nm using a standard curve of $KH_2PO_4$, after adding 0.5 ml. of 1.5% $H_2SO_4$, 0.5 ml. of 3.3% ammonium molybdate and 0.5 ml. of amidol reagent to 3.5 ml. of degrading solution and permitting the sample to stand for 20 minutes at 25° C.

Remarks 3: Lithium content was determined by flame photometry using Jarrell Ash Flame Emission Spectrophotometer Model AA-780; $C_2H_4$(0.4 kg/cm$^2$) 1.75 l/min; air (1.5 kg/cm$^2$), 9.0 l/min; sensitivity, 3.90; wave length, 2708Å.

Remarks 4: Assignment of structure and the binding position of pyrophosphate to the nucleoside by NMR spectroscopy.

The sample nucleoside 5'-phosphate 3'-(2')-phosphates were dissolved in $D_2O$. Proton noise-decoupling $^{13}$C-NMR spectra were obtained at 25.2 MHz on a Varian XL-100-15 spectrophotometer operating in the Fourier transform mode at room temperature. All chemical shifts were calculated relative to an internal reference, dioxane.

Proton-NMR spectra were recorded on the same instrument operating in the Fourier transform mode at 100 MHz. Chemical shifts were recorded from an internal 2,2-dimenthyl-2-silapental-5-sulfonate.

The present invention has further provided a new nucleoside 5'-phosphate (mono, di or tri) 3' (2')-monophosphates, derived from nucleoside 5'-phosphate (mono, di or tri) 3' (2')-diphosphates and the process for the production of these additional nucleosides.

When nucleoside 5'-phosphate (mono, di or tri) 3' (2')-diphosphates are treated in 0.1 N HCl or 0.1 N NaOH in the presence of a barium salt for 1 to 2 hours at 37° C. and purified by combination of adsorption on active carbon, solvent precipitation and ion-exchange resin chromatography, the new nucleoside 5'-phosphate (mono, di or tri) 3' (2')-monophosphates (II) are easily obtained as a white microcrystalline powder, as the result of the release of one phosphate from pyrophosphoryl group at 3'-position of nucleoside 5'-phosphate (mono, di or tri) 3' (2')-diphosphates.

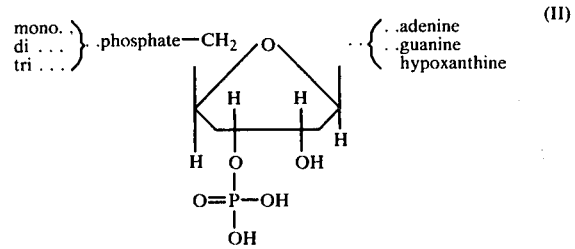

Biological activity of new nucleoside 5'-phosphate (mono, di or tri) 3'-diphosphates and nucleotide pyrophosphotransferase:

The characteristic of the said nucleotide pyrophosphotransferase is that it inhibits the growth of Hela $S_3$, L1210 and L5178Y cells in culture at a relatively low concentration, 5 to 10 units/ml. When these cells are incubated with various concentrations of the purified enzyme obtained from St. adephospholyticus A 4668 in a proper medium, RPMI 1640-20% calf serum for L5178Y and L1210 cells and MEM - 10% calf serum for Hela cells, the growth of cells is markedly inhibited, being accompanied by the inhibition of protein synthesis, as shown in Table 6. Furthermore, antitumor action can be most significantly demonstrated in experimental tumors in mice. For example, when $BDF_1$ mice weighing 18 to 22 grams were intraperitoneally inoculated with $2 \times 10^6$ cells of L1210 cells and the nucleotide and the enzyme was administered intraperitoneally once daily for 10 days consecutively beginning 24 hours after the inoculation, the enzyme and pppApp distinctly suppressed the accumulation of abdominal dropsy without causing toxicity to the mice and prolonged the lifespan as shown in Table 7, but ATP and heat-inactive enzyme are not effective on the tumor-bearing mice. The nucleotide or enzyme is combined with a conventional pharmaceutically acceptable nontoxic carrier for intraperitoneal administration.

Table 6

Effect of purified nucleotide pyrophosphotransferase from St. adephospholyticus A 4668 on the cell growth and protein synthesis

| Enzyme concentration (units/ml.) | cells | Inhibition (% of control) | | | |
|---|---|---|---|---|---|
| | | Cell growth | | | Protein Synthesis |
| | | Hela | L5178Y | L1210 | L1210 |
| 0 | | 0 | 0 | 0 | 0 |
| 1 | | 0 | 9 | 12 | 24 |
| 5 | | 1 | 30 | 29 | 35 |
| 10 | | 25 | 92 | 63 | 59 |

Table 7

Effects of nucleotide and purified nucleotide pyrophosphotransferase on the life span of mice

| Substances | Dose (mg/kg.day) | MST (day) | T/C (%) | 30 days survivors |
|---|---|---|---|---|
| pppApp 7Li | 20 | 16.8 | 189 | 2/5 |
| | 10 | 12.5 | 140 | 1/5 |
| | 5 | 14.0 | 157 | 1/5 |
| ATP 2Na | 20 | 8.6 | 97 | 0/5 |
| | 10 | 9.2 | 103 | 0/5 |
| | 5 | 8.7 | 98 | 0/5 |
| Native enzyme (specific activity 1293) | 2 | 13.4 | 151 | 1/5 |
| | 1 | 13.8 | 155 | 0/5 |
| | 0.5 | 12.2 | 137 | 0/5 |
| Heat-inactive enzyme (no activity) | 2 | 9.8 | 110 | 0/5 |
| | 1 | 10.6 | 119 | 0/5 |
| | 0.5 | 9.0 | 101 | 0/5 |
| Control | — | 8.9 | 100 | 0/10 |

Animal: Male $BOF_1$
Tumor: L1210, Sloan-Kettering line, $10^5$ cells/head, i.p.
MST: Mean survival time The following examples, in which proportions are by weight unless otherwise indicated, illustrate methods of carrying out the present invention, but it is to be understood that they are given for purposes of illustration and not limitation.

EXAMPLE 1

An aqueous medium having the following composition and pH was prepared:

|  | Percent |
|---|---|
| glycerol | 2.0 |
| polypeptone | 4.0 |
| $KH_2PO_4$ | 0.1 |
| $K_2HPO_4$ | 0.1 |
| $MgSO_4 \cdot 7H_2O$ | 0.05 |
| $Mn^{++}$ (as $MnSO_4$) | 2 ppm |
| $Fe^{++}$ (as $FeSO_4$) | 2 ppm |
| pH | 7.0 |

100 ml. of this medium was sterilized at 120° C. in a 500 ml. Sakaguchi-shaking flask which was inoculated with a culture of Streptomyces asperigilloides ATCC 14808, and incubated at 28° C. for 2 days on a shaker. 10 liters of this medium in a 20-liter stainless steel jar fermentor were aseptically inoculated with 1¢ by volume of a growing culture described above. The fermentation was carried out at 28° C. for 40 hours with agitation and aeration. After the mycelia were removed from the cultured broth by filtration, ammonium sulfate was added to the filtrate (1), giving a 60% saturation, the solution was mixed and allowed to stand overnight in the cold. The resulting precipitate (2) was harvested by centrifugation, dissolved in water and dialyzed for 24 hours against running water. Any precipitate that appeared during dialysis was removed by centrifugation. The dialyzed preparation was applied to a DEAE-cellulose column which had been equilibrated with 0.01 M acetate buffer (pH 5.5), and the enzyme passed through the column without retention. The active fraction (3) was applied to a CM-Sephadex C-25 column which had been equilibrated with 0.01 M acetate buffer (pH 5.5) containing 0.001 M $MgCl_2$. After the column was washed with the same buffer, the enzyme was eluted lineally with the same buffer supplemented with 0.1 to 0.5 M NaCl. The active fraction eluted with 0.35 to 0.45 M NaCl (4) was concentrated by the addition of ammonium sulfate (60% saturation). The precipitated enzyme was dissolved in a small amount of 0.01M Tris-HCl buffer (pH 8.7) containing 0.01 M $MgCl_2$, dialyzed sufficiently against the same buffer, and applied to a DEAE-Sephadex A-50 column which had been equilibrated with 0.01 M Tris-HCl (pH 8.7) containing 0.01 M NaCl. After the column was washed with the same buffer, the enzyme was eluted in stepwise fashion with 0.02, 0.05 and 0.15 M NaCl.

The active fraction eluted with 0.05 M NaCl (5) was dialyzed against 0.01 M Tris-HCl buffer (pH 8.7) applied to a hydroxylapatite column which had been equilibrated with the same buffer, and eluted with linear pH gradient (pH 8 to 9) of the buffer.

The active enzyme fraction eluted at pH 9 to 8.7 (6) was then applied to a Sephadex G-75 column which had been equilibrated with 0.05 M glycine-NaOH buffer (pH 9.0) containing 0.01 M $MgCl_2$.

Gel filtration was carried out with the same buffer and a homogeneous enzyme solution (7) was obtained. The results of enzyme purification are presented in Table 8.

Table 8

| Active fraction | Volume (ml.) | Total activity (units) | Total protein ($OD_{280nm}$) | Specific activity | Yield (%) |
|---|---|---|---|---|---|
| (1) | 10000 | 245000 | 252000 | 0.97 | 100 |
| (2) | 600 | 80000 | 32000 | 2.5 | 32.5 |
| (3) | 1500 | 75000 | 7000 | 10.7 | 30.6 |
| (4) | 800 | 65000 | 1850 | 35.2 | 26.5 |
| (5) | 600 | 60000 | 720 | 84.5 | 24.5 |
| (6) | 110 | 33000 | 178 | 186 | 13.5 |
| (7) | 45 | 19500 | 25 | 780 | 8.0 |

EXAMPLE 2

Streptomyces morookaensis ATCC 19166 and Actinomyces violascens ATCC 23968 were cultivated separately under the conditions of Example 1. In each case, 1000 ml. of culture filtrate was treated according to the purification procedures of Example 1, and the purified enzymes were obtain as shown in Table 9.

Table 9

| Strain No. | | Actinomyces violascens ATCC 23968 | Streptomyces morookaensis ATCC 19166 |
|---|---|---|---|
| Filtrate | Total activity | | |
| | (units) | 31000 | 42500 |
| | Specific activity | 0.81 | 0.58 |
| Purified enzyme: | Total activity | | |
| | (units) | 2050 | 3650 |
| | Yield (%) | 6.6 | 8.6 |
| | Specific activity | 1100 | 960 |

EXAMPLE 3

An enzyme reaction mixture having the following composition was prepared:

| 0.25M Tris-HCl buffer (pH 9.0) | 160 ml. |
|---|---|
| 0.05M $MgCl_2$ | 20 ml. |
| ATP . 2N | 2.5 g |
| Distilled water | 20 ml. |
| Total | 200 ml. |

A small collodion bag containing 10 ml. of purified enzyme solution (specific activity: 274, total units: 465) which was obtained from Streptomyces morookaensis ATC 19166 was placed in the reaction mixture described above, and incubated at 30° C. for 24 hours with stirring.

100 ml. of the reaction mixture was diluted to twice the volume adjusted to pH 7.8 with HCl, and adsorbed on a DEAE-Sephadex A-25 (3 × 55 cm) column which had been equilibrated with 0.01 M Tris-HCl buffer (pH 7.8). The column was washed with the same buffer and then pppApp was eluted with a salt linear gradient of 0.15 to 0.35 M LiCl in the same buffer.

No. 95 to 124 fractions (20 ml. each) eluted with the salt concentrations of 0.22 to 0.25 M were pooled, concentrated at 37° to 42° C. in vacuo, and then precipitated by the addition of 5 volumes of acetone:ethanol mixture (1:1 by volume). A pppApp Li salt was washed with 95% by volume ethanol five times, and 1.55 g of this salt was obtained after drying in vacuo.

EXAMPLE 4

The reaction mixture consisted of 250 mM glycine-NaOH buffer (pH 10.0), 6.0 ml.; 100 mM ATP, 2.0 ml.; 50 mM $MgCl_2$, 4.0 ml.; 100 mM pyrophosphate acceptor indicated in Table 10, 2.0 ml.; distilled water, 4.0 ml.; and enzyme solution obtained from the various purification steps of the culture broth of Streptomyces aspergilloides ATCC 14808, 6.0 ml. The reaction mixture was incubated at 37° C. for two hours, adsorbed on a Dowex 1 × 4, Cl type, column (1.7 × 25 cm) which had been equilibrated with 0.01 M NaCl in 0.01 N HCl, and then eluted with a linear gradient from 0.01 to 0.5 M NaCl in 0.01 N HCl. Fractions eluted at the concentrations of 0.2 to 0.25 M NaCl were pooled, adjusted to pH 7 with 0.1 N NaOH, and readsorbed on a DEAE-Sephadex A-25 (2.2 × 25 cm) column which had been equilibrated with 0.01 M Tris-HCl buffer (pH 7.5). By eluting with 0.1 to 0.3 M LiCl, fractions having an optional density of 260 nm were pooled, concentrated 37° C. in vacuo, and white precipitate was obtained by the addition of 10 volumes of 99% by volume ethanol. The precipitate was dissolved in a small amount of water and 5 volumes of 90% by volume ethanol were added thereto to reprecipitate the precipitate. After drying the reprecipitated precipitate in vacuo, nucleotide lithium salt was obtained as indicated in Table 10.

were concentrated to one twentieth by volume at 37° C., in vacuo and precipitated by addition of 5 volumes of cold acetone:ethanol mixture (9:1 by volume). After several washings with the same mixture and drying in vacuo, 70.5 mg of ppApp.6Li and 142 mg of pppApp.7Li were obtained as white microcrystalline powder.

EXAMPLE 6

Reaction mixture consisting of 250 mM glycine-NaOH buffer (pH 10.0), 6.0 ml.; 50 mM ATP, 4.0 ml.; 50 mM GMP, 4.0 ml.; 50 mM MgCl$_2$, 4.0 ml. and the enzyme solution (specific activity: 150, 3 units/ml.) obtained from Streptoverticillium septatum ATCC 27464, 6.0 ml. was incubated at 37° C. for 4 hours, applied to a Dowex 1 × 4, Cl type, column (1.7 × 20 cm), and then eluted with a linear gradient from 0.01 to 0.5 M NaCl in 0.01 N HCl. Fractions eluted between 0.21 and 0.24 M NaCl were pooled, neutralized with 0.1 N NaOH, and adsorbed on a DEAE-Sephadex A-25 column (2.2 × 25 cm) which had been equilibrated with 0.05 M Tris-HCl buffer (pH 7.5). 200 ml. of pGpp fraction eluted with 0.1 to 0.3 M LiCl were concentrated to 10 ml. in vacuo, and Table 10

| Enzyme sources | Spcific activity | Photphate donor | Phosphate acceptor | Main product | Yield (mg as lithium salt) |
|---|---|---|---|---|---|
| Purified enzyme | 650 | ATP | ATP | pppApp | 115 |
| " | " | ATP | ADP | ppApp | 87 |
| " | " | ATP | GTP | pppGpp | 135 |
| " | " | ATP | GDP | ppGpp | 120 |
| " | " | ATP | ITP | pppIpp | 62 |
| " | " | pppApp | AMP | pApp | 85 |
| Culture filtrate | 0.21 | ATP | ATP | pppApp | 75 |
| DEAE-cellulose chromatography active fraction | 1.95 | ATP | ATP | pppApp | 125 |
| CM-Sephadex chromatography active fraction | 53.5 | ATP | ATP | pppApp | 108 |
| DEAE-Sephadex chromatography active fraction | 182 | ATP | ATP | pppApp | 132 |
| " | " | dATP | GDP | ppGpp | 86 |
| " | " | ATP | GTP | pppGpp | 125 |
| " | " | ATP | GMP | pGpp | 74 |
| " | " | pppApp | GMP | pGpp | 26 |
| | | | | pApp | 38 |

EXAMPLE 5

Purified enzyme was obtained from the culture filtrate of Streptomyces adephospholyticus A 4668, which was cultivated under the fermentation conditions of Example 1, according to the methods described in Example 1. 20 times volumetric diluent of this purified enzyme (specific activity: 1500, 60 units/ml.), 6.0 ml., was incubated with 5 ml. of 1 M Tris-HCl buffer (pH 10.0), 500 mg of ATP.2Na, 100 mg of ADP.2Na, 5.0 ml. of 0.05 M MgCl$_2$ and 10 ml. of distilled water, for two hours at 37° C. During the enzyme reaction, pH was controlled at 8.5 by addition of 1 N NaOH. The reaction mixture was applied to a DEAE-Sephadex A-25 column (2.2 × 25 cm) which had been equilibrated with 0.01 M Tris-HCl buffer (pH 7.2), eluted with a linear gradient from 0.1 to 0.3 M LiCl in the same buffer, and fractionated every 15 ml. Resulting pppApp and ppApp fractions were concentrated to one twentieth by volume in vacuo and added thereto were 5 volumes of cold acetone:ethanol mixture (9:1 by volume). About 250 mg of the precipitate obtained by filtration were dissolved in 100 ml. of water, adsorbed on a DEAE-Sephadex A-25 columm (1.8 × 35cm), and then eluted with 0.15 to 0.35 M LiCl solution. pppApp and ppApp fractions added thereto were 10 volumes of 99% by volume ethanol. The resultant precipitate of pGpp lithium salt was dissolved in a small amount of water, and reprecipitated with 90% by volume ethanol. After drying in vacuo, 56.2 mg of pGpp.5Li were obtained as white microcrystalline powder.

EXAMPLE 7

200$\mu$ mole of ATP or dATP and 200$\mu$ mole of various nucleotides were incubated using the purified enzyme, the reaction mixture composition and the reaction conditions described in Example 4. Each nucleotide was recovered from the reaction mixture according to the methods for isolation and purification of Example 5 and 6. Main reaction products and their yield are shown in Table 11.

Table 11

| Phosphate donor | Phosphate acceptor | Main product | Yield (mg as Li salt) |
|---|---|---|---|
| ATP | ATP | pppApp | 132 |
| " | ADP | ppApp | 105 |
| " | GTP | pppGpp | 140 |
| " | GDP | ppGpp | 130 |
| " | GMP | pGpp | 52.5 |
| " | ITP | pppIpp | 74.2 |
| " | IDP | ppIpp | 25.6 |

Table 11-continued

| Phosphate donor | Phosphate acceptor | Main product | Yield (mg as Li salt) |
|---|---|---|---|
| dATP | GTP | pppGpp | 92.5 |
| " | ADP | ppApp | 69.3 |
| pppApp | GMP | pGpp | 22.5 |
|  |  | pApp | 18.3 |

EXAMPLE 8

20 mg of each nucleoside 5'-phosphate (mono, di or tri) 3'-diphosphates lithium salts obtained in Example 7 was weighed, dissolved in 20 ml. of 0.25 N HCl, and the solution was allowed to stand at 37° C. for one hour. After being neutralized with 0.5 N KOH solution, the solution was refined by the methods of ion-exchange resin column chromatography, adsorption onto active carbon, and solvent precipitation as described in Examples 1 and 2, which resulted in white microcrystalline powders of lithium salts as follows:

Table 12

| Starting materials | Products | Yield (mg as Li salt) |
|---|---|---|
| pppApp | ppAp | 11.2 |
| ppApp | ppAp | 13.8 |
| pppGpp | pppGp | 9.8 |
| ppGpp | ppGp | 7.5 |
| pGpp | pGp | 6.3 |
| pppIpp | pppIp | 4.6 |

What is claimed is:

1. A purine nucleoside 5'-(mono, di or tri) phosphate 3'(2')-diphosphate and the corresponding purine nucleoside 5'-(di or tri) phosphate 3'(2')-monophosphate and the salts thereof selected from the group consisting of
   adenosine-5'-monophosphate 3'(2')-diphosphate(pApp),
   adenosine-5'-diphosphate 3'(2')-diphosphate(ppApp),
   adenosine-5'-triphosphate 3'(2')-diphosphate(pppApp),
   guanosine-5'-monophosphate 3'(2')-diphosphate(pGpp),
   inosine-5'-monophosphate 3'(2')-diphosphate(pIpp),
   inosine-5'-diphosphate 3'(2')-diphosphate(ppIpp),
   inosine-5'-triphosphate 3'(2')-diphosphate(pppIpp),
   $\beta,\gamma$-methylene adenosine 5'-triphosphate 3'(2')-diphosphate(p(CH$_2$)ppApp),
   guanosine-5'-triphosphate 3'(2')-monophosphate(pppGp),
   inosine-5'-diphosphate 3'(2')-monophosphate(ppIp),
   inosine-5'-triphosphate 3'(2')-monophosphate(pppIp),
   $\beta,\gamma$-methylene adenosine-5'-triphosphate 3'(2')-monophosphate(p(CH$_2$)ppAp) and
   $\beta,\gamma$-methylene guanosine-5'-triphosphate 3'(2')-monophosphate(p(CH$_2$)ppGp)
and lithium, potassium and sodium salts thereof.

2. A pharmaceutical composition for intraperitoneal administration to animals comprising a substance according to claim 1 in a concentration sufficient to suppress an accumulation of abdominal dropsy without causing toxicity to the recipient in vivo in combination with a pharmaceutically acceptable nontoxic carrier.

3. A method for chemotherapeutically treating an animal bearing ascites tumor including an accumulation of abdominal dropsy, which comprises administering a compound according to claim 1 to said animal in a dosage sufficient to lower said accumulation without causing toxicity to said animal.

4. A pharmaceutical composition of claim 2 wherein said animals are rodents.

5. A method of claim 3 wherein said animal is a rodent.